(12) United States Patent
Riihimaa

(10) Patent No.: US 11,324,206 B2
(45) Date of Patent: May 10, 2022

(54) APPARATUS AND A METHOD FOR GROWING INVERTEBRATES

(71) Applicant: Entoprot Oy, Oulu (FI)

(72) Inventor: Ari Riihimaa, Oulu (FI)

(73) Assignee: Entoprot Oy, Oulu (FI)

(*) Notice: Subject to any disclaimer, the term of this patent is extended or adjusted under 35 U.S.C. 154(b) by 7 days.

(21) Appl. No.: 17/052,593

(22) PCT Filed: May 3, 2019

(86) PCT No.: PCT/FI2019/000007
§ 371 (c)(1),
(2) Date: Nov. 3, 2020

(87) PCT Pub. No.: WO2019/211511
PCT Pub. Date: Nov. 7, 2019

(65) Prior Publication Data
US 2021/0235675 A1    Aug. 5, 2021

(30) Foreign Application Priority Data

May 4, 2018  (FI) ...................................... 20187064

(51) Int. Cl.
*A01K 67/033* (2006.01)
*A01K 1/00* (2006.01)

(52) U.S. Cl.
CPC .............. *A01K 67/033* (2013.01); *A01K 1/00* (2013.01)

(58) Field of Classification Search
CPC .................................. A01K 67/033; A01K 1/00
See application file for complete search history.

(56) References Cited

U.S. PATENT DOCUMENTS

| 3,601,461 A | 8/1971 | Melcher |
| 4,334,498 A * | 6/1982 | Bedding ................ A01N 63/12 |
| | | 119/6.7 |

(Continued)

FOREIGN PATENT DOCUMENTS

| CN | 102885010 A | 1/2013 |
| CN | 108391629 A * | 8/2018 |

(Continued)

OTHER PUBLICATIONS

International Search Report for Priority Document PCT/FI2019/000007.

(Continued)

*Primary Examiner* — Monica L Barlow
*Assistant Examiner* — Aaron M Rodziwicz
(74) *Attorney, Agent, or Firm* — Jacob Eisenberg

(57) ABSTRACT

As set out in this disclosure, the growing surface of invertebrates is increased and circumstances for the invertebrate are optimized by a growing apparatus that includes a rotatable casing and a growing chamber inside the casing. Inside the casing is at least one growing platform and the growing platform comprises one or more growing plates. The growing platform is configured in such a way that the growing plate can be kept in the same position even when the casing is rotated. This enables mixing the added food and other compounds in the growing chamber and thus prevents the food layers from becoming too thick while at the same time provides an undisturbed environment for the invertebrates.

14 Claims, 7 Drawing Sheets

(56) References Cited

U.S. PATENT DOCUMENTS

| | | | | |
|---|---|---|---|---|
| 10,058,080 B2* | 8/2018 | Leo | .................... | A23K 20/174 |
| 2015/0296760 A1* | 10/2015 | Perednia | .............. | A01K 67/033 |
| | | | | 119/6.5 |

FOREIGN PATENT DOCUMENTS

| | | | | | |
|---|---|---|---|---|---|
| CN | 110178796 A | * | 8/2019 | | |
| FR | 3070001 A1 | * | 2/2019 | ............. | A23K 50/90 |
| FR | 3070002 A1 | * | 2/2019 | ........... | A01K 67/033 |
| JP | 2013039052 A | | 2/2013 | | |
| WO | WO2017198895 A1 | | 11/2017 | | |
| WO | WO-2018169398 A1 | * | 9/2018 | ........... | A01K 67/033 |
| WO | WO-2020129058 A1 | * | 6/2020 | ............. | B07B 13/04 |
| WO | WO-2020246879 A1 | * | 12/2020 | ............. | B65G 51/01 |
| WO | WO-2020255121 A1 | * | 12/2020 | ............... | B09B 3/00 |

OTHER PUBLICATIONS

Written Opinion for Priority Document PCT/FI2019/000007.
JP2013039052 (A) English Language Translation.
CN102885010 (A) English Language Translation.

* cited by examiner

APPARATUS AND A METHOD FOR GROWING INVERTEBRATES

CROSS REFERENCE TO RELATED APPLICATIONS

This application is a national phase of International Application No.: PCT/FI2019/000007, filed on 3 May 2019, which claims priority to Finnish Patent Application FI20180007064 filed on May 4, 2018. The contents of the above-references applications are expressly incorporated herein by reference to their entireties.

BACKGROUND OF THE INVENTION

The present disclosure relates to an apparatus for growing invertebrates that breathe gas comprising a casing having a first end of the casing and a second end of the casing, a growing chamber inside said casing and at least one growing platform in the growing chamber. The present disclosure also relates to a method for growing invertebrates.

Many invertebrates could be grown in artificial surroundings by placing them directly within a suitable food source. This food source is consumed by the invertebrates. When the invertebrates have grown enough, they are removed from their growing space and they are processed. The invertebrates, for example different kinds of larvae or worms, can be used in many ways. One possibility is to use them as a protein source for animals or humans. This could be quite beneficial because many invertebrates have the ability to consume a wide range of organic materials and convert them into invertebrate matter. This process is quite efficient and opens up many possibilities. However, there have been as of yet only a few attempts to do this on an industrial scale.

The conventional methods for growing invertebrates for example such as insect larvae have typically involved the use of flat trays or similar vessels. One example is disclosed in the patent publication US 2013/0319334. In this patent larvae are placed in the trays and food is added to the surface of the food mass and larvae. Because many invertebrates must have an adequate supply of air, they tend to stay near the surface of the food layer. Even if the invertebrate to be grown is an anaerobic variety, the heat inside the food mass could grow too high for the invertebrate to flourish. Also, there could be many unwanted processes in the food layer areas without air, such as fermentation. This means that to allow effective feeding and growth the food layer must not exceed some height that depends on the composition of the food matter and the abilities and traits of the invertebrates. This also means that to achieve optimal or near-optimal growing conditions, only a certain maximal number of invertebrates can be grown per a certain area of the growing chamber or other surface on which the mass of food and invertebrates reside during the growing process. Attempts have been made to circumvent these problems by introducing methods to mix the food layer for example by turning or moving the trays or containers. However even using such a method will not eliminate areas that are not optimal for the invertebrate to grow if the food layer is too thick. Also, unnecessary moving of the invertebrate inside the growing facility may not be optimal when aiming to provide for good environment for the invertebrate.

BRIEF SUMMARY OF THE INVENTION

An object of the present disclosure is a solution that can significantly reduce the disadvantages and drawbacks of the prior art. In particular, the object of the present disclosure is a solution that allows growing invertebrate on a commercial scale.

The objects of the present disclosure are attained with an arrangement that is characterised by what is stated in the independent patent claims. Some advantageous embodiments of the present disclosure are disclosed in the dependent claims.

The inventor found out that moving the invertebrates disturbs their feeding and thus can slow down their progress and growing.

In the present disclosure the growing surface of an apparatus for growing invertebrates is increased and the circumstances for the invertebrates are optimized by a growing apparatus that comprises a rotatable casing and a growing chamber inside the casing. Inside the casing is at least one growing platform. The growing platform comprises one or more growing plates and the growing platform is configured to be rotated in such a way that the growing plate can be kept in the same position even if the casing is rotated. This enables mixing the added food and other compounds in the growing chamber and thus prevents food layers from becoming too thick and at the same time it provides an undisturbed environment for the invertebrates. The rotations of the growing platform and the casing can be synchronized in such a way that the growing plate is in the same position even if the casing is rotated. This synchronization may be done in some phase of the growing process or during whole time of the growing process.

The apparatus according the present disclosure is especially suitable for invertebrates that use spiracles and tracheae for gas exchange, i.e. they need air, but it is also applicable to other kinds of invertebrates. By 'needing air', it is meant that the invertebrates breathe gas, i.e. their respiratory systems are incompatible with liquid environments. Invertebrate groups that are suited for growing with the present disclosure, but are not limited to these, are arthropods, rheumatoid worms and nematodes. It must be noted that 'growing' is not limited to whole life span of an invertebrate, but it could include one or more life stages or part of them. An example of this are the larval stages of a fly.

When reference is made in the text to the upper or the lower parts or respective directions, a situation is described in which the apparatus according to the present disclosure is in its normal deployed configuration.

In one embodiment of the present disclosure an apparatus for growing invertebrates that breathe gas comprises a casing having a first end of the casing and a second end of the casing, a growing chamber inside said casing and at least one growing platform in the growing chamber. In one advantageous embodiment of the present disclosure the casing and the growing platform are rotatable, and the rotation axis is between the first end of the casing and the second end of the casing, and the growing platform extends from the first end of the casing to the second end of the casing or either end of the casing. The growing platform therefore extends from either end of the casing or from both ends of the casing into the growing chamber. The growing platform comprises one or more growing plates having a first end of the growing plate, a second end of the growing plate, a first growing plate surface and a second growing plate surface. The first growing plate surface is configured to be a growing surface for invertebrates and the growing platform is configured in such a way that the first growing plate surface can be kept facing upwards even if the casing is rotated. Advantageously the growing plates can be arranged in such a way that when a suitable amount of food is spread over them, spaces for air or air flow remain that air can pass through the contents composed of growing plates, food and invertebrate. The arrangement is such that rotating the casing mixes the contents on of the bottom of the growing chamber and spreads it over the walls where it can drip onto the growing plates. By rotating the growing platform, the growing plate can be in the same position even if they circulate the rotation axis of the casing. It must be noted that rotating does not mean that the casing or the growing platform must make full turns. They can also change direction and stop intermittently.

In one embodiment of the apparatus according to the present disclosure, the growing platform comprises a growing platform shaft that extends at least from the first end of the casing to the second end of the casing or from either end of the casing into the growing chamber, and at least one growing plate is fixed to the growing platform shaft.

In a second embodiment of the apparatus according to the present disclosure, the growing platform comprises two growing platform shafts: a first growing platform shaft and a second growing platform shaft, and the first growing platform shaft is at the first end of the casing and the second growing platform shaft is at the second end of the casing and at least one growing plate is fixed between the first growing platform shaft and the second growing platform shaft.

In a third embodiment of the apparatus according to the present disclosure, on the first growing plate surface is a shape or shapes, such as grooves or recesses or similar, for keeping invertebrates on the growing surface.

In a fourth embodiment of the apparatus according to the present disclosure, the casing is an elongated structure, i.e. the longitudinal axis of the casing is longer than the diameter of the casing, and the rotation axis of the casing is parallel to the longitudinal axis of the growing platform or growing platforms. Also, the rotational axis of the growing platform is parallel to the rotation axis of the casing.

In a fifth embodiment of the apparatus according to the present disclosure, there is a locking arrangement to fix the growing platform shaft to be immobile in relation to the casing in such a way that the first growing plate surface keeps facing upwards when the casing is rotated.

In a sixth embodiment of the apparatus according to the present disclosure, the apparatus comprises a casing rotating arrangement and a growing platform moving arrangement, and the casing rotating arrangement and the growing platform moving arrangement are synchronized in such a way that the first growing plate surface keeps facing upwards when the casing is rotated.

In a seventh embodiment of the apparatus according to the present disclosure, air or some other gas is arranged to be blown into the growing chamber in such a way that the gas flow is tracking at least some part of the first growing plate surfaces.

In an eighth embodiment of the apparatus according to the present disclosure, some parts of the inner surface of the casing form the growing chamber inner wall and on the inner surface of the casing are one or more mixing arrangements, such as flanges or similar, which are configured to mix and lift the food for the invertebrates from the bottom of the growing chamber when the casing is rotated.

In a ninth embodiment of the apparatus according to the present disclosure, the apparatus comprises a central shaft that is at least partly hollow, and the central shaft is arranged to transport at least water into the growing chamber. In some embodiments the central shaft can be used to inject food or other materials that are required in the growing process.

In a tenth embodiment of the apparatus according to the present disclosure, at least part of the first end of the casing or the second end of the casing or both are movable in relation to the rest of the casing and at least one growing platform is fixed to at least one said movable part of the end of the casing. These movable parts can be kept immobile when the rest of the casing is rotated, and because the growing platform is fixed to the movable part, the first growing plate surface is kept facing upwards. Of course, the growing plate can be set to another position.

In an eleventh embodiment of the apparatus according to the present disclosure, the growing plate is configured to be turn able at least to a position where the growing plate surfaces are vertical. In a twelfth embodiment of the apparatus according to the present disclosure, the growing platform is configured to follow the rotation of the casing and the growing plate is configured to be turned when the growing platform is in a lower position in relation to the casing. In that kind of embodiments, the growing plate can scoop material from the bottom of the growing chamber on the first growing plate surface.

A method for growing invertebrates that breathe gas according to an embodiment uses steps where food is injected into a growing chamber where the first growing plate surfaces are kept in an upward-facing position to increase the inner surface area of the growing chamber, the invertebrates to be grown are added to the growing chamber before, during or after injecting the food, and the casing is rotated so that the food will spread at least partly over the surfaces of the inner wall of the growing chamber and drip onto the first growing plate surfaces. An apparatus that is described before, is used in the method.

It is an advantage of the present disclosure that it increases the amount of the invertebrates that can grow in a certain volume of a growing chamber compared to the conventional methods. The means that the present disclosure makes it possible to use the floor area or 3-dimensional space of the production facility efficiently. It also provides an efficient way to mix the food inside the growing chamber and at the same time provides an undisturbed area for the invertebrates to feed and grow.

It is a further advantage of the present disclosure that less manual labour is required.

It is a further advantage of the present disclosure that it improves the growing process by providing the invertebrates a tranquil environment. It also prevents the formation of anaerobic areas in the food layer. It is easier to arrange the measurement and adjustment of various environmental variables such as temperature and concentrations of chemical substances and gasses. Also heat-control and washing the growing chamber and its contents are easier.

It is a further advantage of the present disclosure that it removes the need for constant observation.

An advantage is also that the present disclosure can easily be modified for different species of invertebrates that require different growing conditions. The present disclosure also prevents the invertebrates from drowning in the food. Also, the same device can be used for different life stages of invertebrates.

BRIEF DESCRIPTION OF THE SEVERAL VIEWS OF THE DRAWINGS

In the following, the present disclosure is described in detail. The description refers to the accompanying drawings, in which.

DETAILED DESCRIPTION OF THE INVENTION

The embodiments in the following description are given as examples only and someone skilled in the art can carry out the basic idea of the present disclosure also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the present disclosure may thus be provided.

Figure 1:
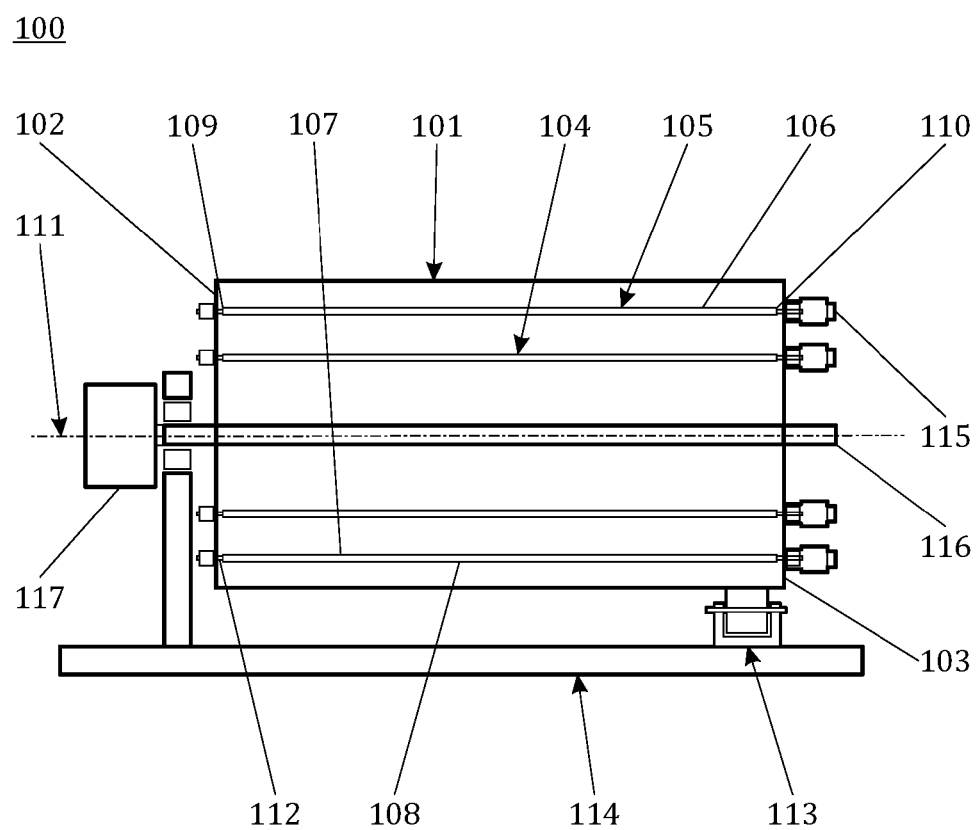
FIG. 1 shows an example of an apparatus according to the present disclosure.

FIG. 1 shows a schematic cross-section in a longitudinal direction of an apparatus 100 in accordance with an embodiment. The apparatus comprises a casing 101 and a growing chamber 104 inside said casing and at least one growing platform 105 in the growing chamber. In this embodiment the apparatus is configured to place on a surface 114. Of course, the apparatus could be placed, for example, on another apparatus.

The casing 101 is a structure that defines and protects the growing chamber 104. In this embodiment, the casing is an elongated construction. The casing has a first end of the casing 102 and a second end of the casing 103 and a wall. The casing is rotatable, and the rotation axis 111 is between the first end of the casing and the second end of the casing. On the rotation axis is a central shaft 116 that is partly hollow. The rotation mixes the food inside the growing chamber and prevents anaerobic areas forming in the food mixture.

Advantageously, the wall of the casing covers the growing chamber from every direction. In the wall of the casing, there could be hatches or windows for inspection the inside of the growing chamber or other maintenance duties. This makes it possible to rotate the casing without the invertebrates being able to escape or fall out. Also, the microbiological control of the growing chamber is easier when it is closed. Of course, the casing and the growing chamber could be constructed in such a way that it is partly open. The apparatus also comprises a casing rotation arrangement 113. The casing rotation arrangement is in this example on the surface 114 below the casing and it comprises several rolls and a motor for rotating said rolls. The casing rests on the rolls and the casing is configured in such a way that when the rolls rotate the casing rotates too. There are arrangements that support and guide the rotating casing. The central shaft could be one of those. Of course, the casing rotating arrangement can be implemented many ways.

In this embodiment the growing platform 105 comprises one or more growing plates 106 and a growing platform shaft 112. The growing platform 105 or the growing platform shaft extends from the first end of the casing 102 to the second end of the casing 103 or either end of the casing 101. The growing platform can therefore implement an extension from either end or from end to end. The growing platform comprises one or more growing plates 106 having a first end of the growing plate 109, a second end of the growing plate 110, a first growing plate surface 107 and a second growing plate surface 108. The growing plate is fixed to the growing platform shaft or between two growing platform shafts. Of course, the growing platform can also be implemented without growing platform shafts.

When the casing 101 is rotated, it mixes the invertebrates, the added food and other compounds in the growing chamber 104. During the rotation of the casing the mixture of invertebrates and wet food adheres to surfaces on the bodies, which helps to spread the mixture over a large area. The shape of the growing plates 106 in the growing chamber is such that at least one side of each plate is flat or curving gently, and there is a mechanism that keeps the flat side up and horizontal while the casing is turning or rotating. Owing to this arrangement, there are surface areas in the growing chamber where the invertebrates can rest and concentrate on feeding, i.e. they are not in a continuous falling movement when the chamber is rotating. At the same time, this arrangement enables mixing the invertebrates, the added food and other compounds in the growing chamber.

Advantageously the growing plate 106 is an elongated broad structure. The first growing plate surface 107 is configured to be a growing surface for invertebrates. The growing platform is configured in such a way that the first growing plate surface can be kept facing upwards even if the casing is rotated. This keeps the invertebrates on the growing plate and therefore on the growing surface. The movements of the casing, when the food is mixed, therefore does not disturb the invertebrates on the growing plate. On the first growing plate surface, there is a shape or shapes, such as grooves or recesses or similar, for keeping invertebrates on the growing surface. There can also be some border structures on the first growing plate surface.

The apparatus 100 comprises a growing platform moving arrangement 115. The casing rotating arrangement 113 and the growing platform moving arrangement are synchronized in such a way that the first growing plate surface 107 keeps facing upwards when the casing is rotated i.e. the growing platform moving arrangement rotates the growing platform. In some embodiments there is a locking arrangement to fix the growing platform shaft 112 to be immobile in relation to the casing 101 in such a way that the first growing plate surface keeps facing upwards when the casing is rotated. In this embodiment there are several growing platforms 105 and each one has its own growing platform moving arrangement. There are embodiments where one growing platform moving arrangement controls all growing platforms. There can be embodiments where there is one growing platform 105 comprising several growing plates 106.

There are embodiments where the growing plate 106 is configured to be rotatable at least to a position where the growing plate surfaces are vertical. This can be used for emptying the first growing plate surfaces 107. In some embodiments, the growing platform is configured to follow the rotation of the casing 101 and the growing plate is configured to be turned when the growing platform is in a lower position in relation to the casing. This can used for consuming food and other materials from the bottom of the growing chamber 104 onto the first growing plate surface.

The rotational axis of the growing platform 105 is parallel to the rotational axis of the casing 101.

In one embodiment there is a container 117 that is attached to the hollow central shaft 116. Food or water or both can be injected from the container via the central shaft into the growing chamber 104. Of course, air or other gas can be injected into the growing chamber in the same way. The gas can be blown in such a way that the gas flow is tracking at least some part of the first growing plate surfaces 107.

FIG. 2 shows a cross-section of an apparatus 100 described in FIG. 1. The cross-section of the casing 101 is circular. In this embodiment, the casing rotating arrangement 113 comprises three rolls that rotate the casing. The casing is rotated around the rotation axis 111. The casing is rotated by a casing rotation arrangement 113. The growing plates 106 are fixed to the growing platforms, which are in turns fixed to the casing and more specifically either end of the casing (or both). The growing platforms are configured in such a way that even when the casing rotates, the growing plates remain in a horizontal position, i.e. the first growing plate surface is upwards, and the second growing plate surface is facing downwards. This can be done by, for example, using the growing platform moving arrangements for rotating the growing platforms.

Figure 2A:
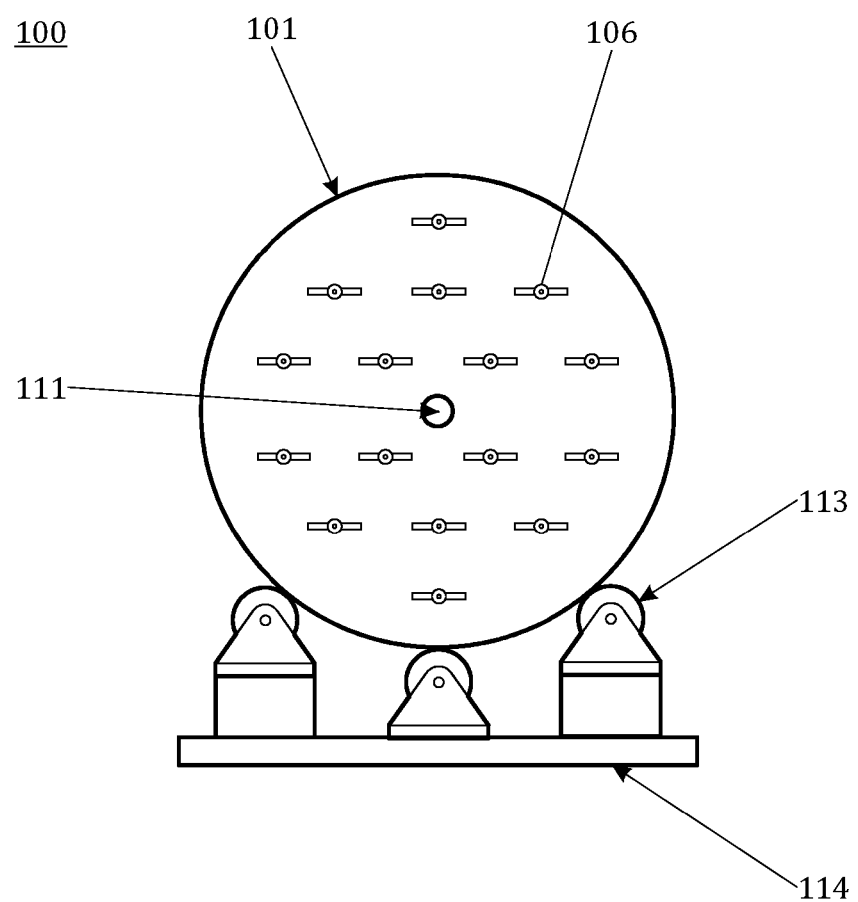
FIG. 2A shows a cross section of the apparatus of FIG. 1, when the casing is in one position.
Figure 2B:
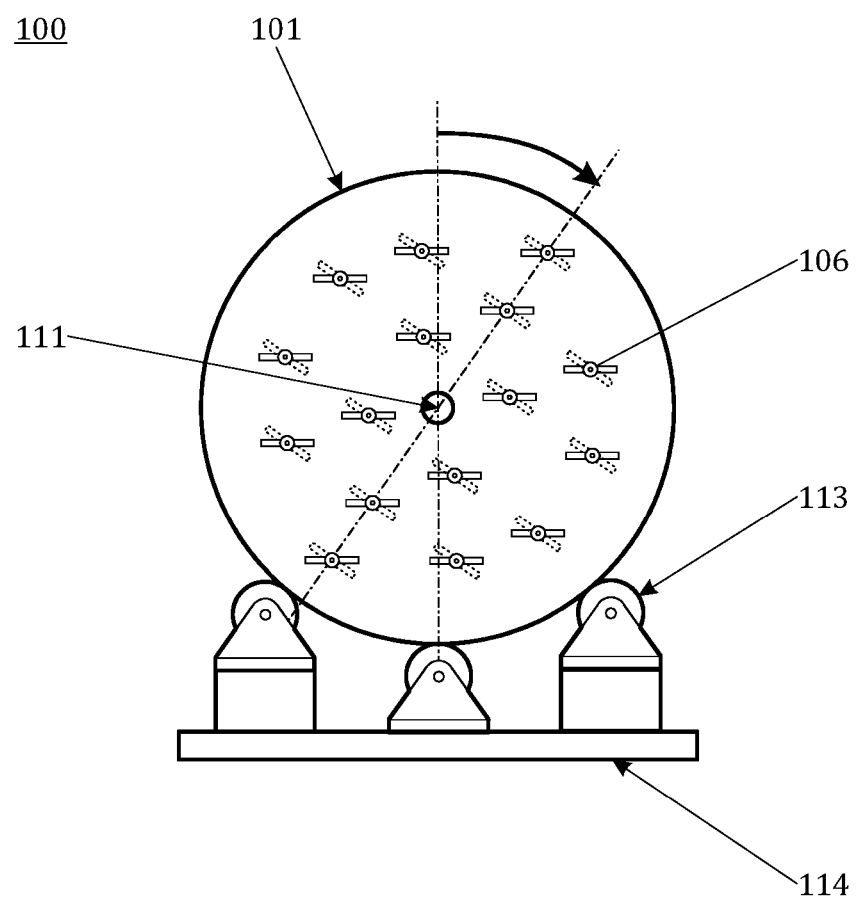
FIG. 2B shows a cross section of the apparatus of FIG. 1, when the casing is in another position.

In FIG. 2A the casing is in one position. The growing plates are in a horizontal position. In FIG. 2B the casing 101 has rotated to another position. The fixing points of the growing platforms move with the casing. The growing platform moving arrangements compensate this movement and rotate the growing platforms so that the growing plates remain in a horizontal position. Longitudinal axis of the growing platforms is parallel to the longitudinal axis of the casing. Similarly, rotational axis of the growing platforms is parallel to the rotational axis of the casing. The growing platforms are placed around the central shaft i.e. the rotational axis of the casing. Because the growing platforms are fixed to the ends of the casing (or either end of the casing), they circulate the rotational axis of the casing. The synchronized rotation of the growing platforms and the casing keep the growing plates in a horizontal position when the casing rotates. Of course, the growing platforms can be set on some another position, for example they can be turned in a vertical position (i.e. the growing plate and its surfaces are vertical) for dropping the invertebrates to the bottom of the growing chamber.

Figure 3:
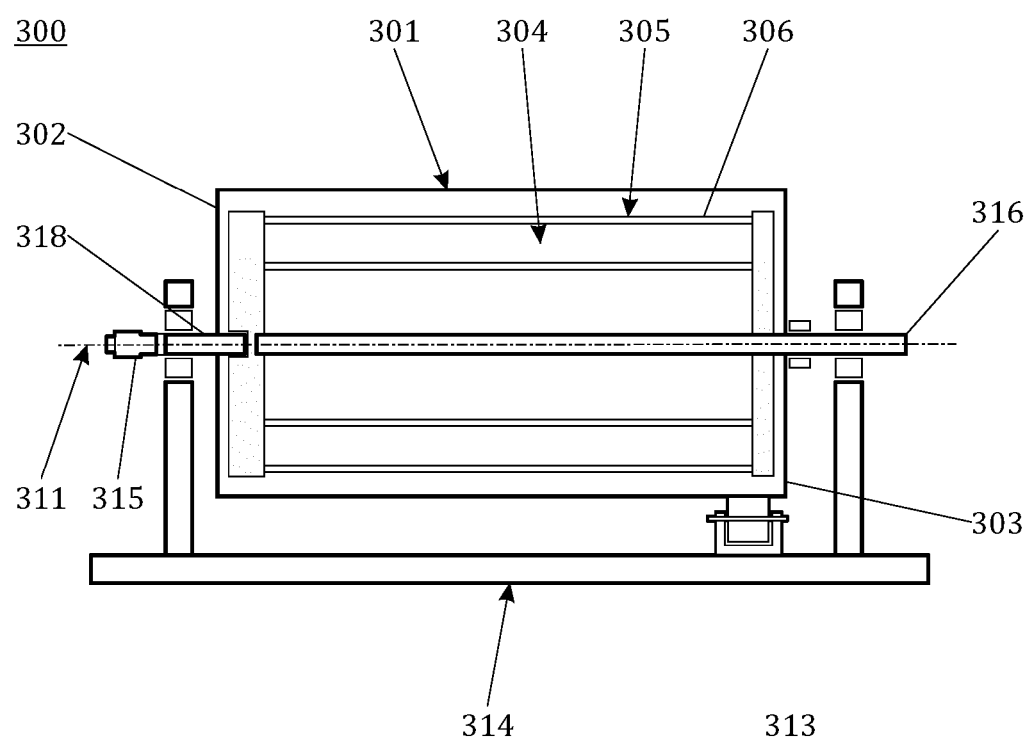
FIG. 3 shows another example of an apparatus according to the present disclosure.

FIG. 3 shows a longitudinal cross section of an apparatus 300 according to another embodiment. The apparatus comprises a casing 301 and a growing chamber 304 inside said casing and a growing platform 305 in the growing chamber. In this embodiment, the apparatus is placed on a surface 314. The casing has a first end of the casing 302 and a second end of the casing 303 and a wall. The casing is rotatable and the rotation axis 311 is between the first end of the casing and the second end of the casing. On the rotation axis is a central shaft 316 that is partly hollow.

The growing platform 305 comprises a multitude of growing plates 306 and a growing platform rotating shaft 318. The central shaft 316 is also part of the growing platform. The growing platform extends from the first end of the casing 302 to the second end of the casing 303. For rotating the growing platform there is a growing platform moving arrangement 315. The growing plates have growing surfaces.

When the casing 301 is rotated, the growing platform 305 is rotated by the growing platform moving arrangement 315 in such a way that the upward position of the growing surfaces is maintained. There are also embodiments where the apparatus 300 comprises a locking arrangement. The locking arrangement fixes the growing platform to be immobile in relation to the casing in such a way that the first growing plate surface keeps facing upwards when the casing is rotated.

FIG. 4 shows a cross section of an apparatus 300 described in FIG. 3. The cross section of the casing 301 is circular. In this embodiment, the casing rotating arrangement 313 comprises three rolls that rotate the casing. The casing is rotated around the rotation axis which is congruent to the central shaft 316. The growing plates 306 are fixed to the growing platform. The growing platform is configured in such a way that even when the casing rotates, the growing plates remain in a horizontal position, i.e. the first growing plate surface keeps facing upwards, and the second growing plate surface faces downwards.

There is a mixing arrangement 319 that is fixed to an inner wall of a growing chamber 304. The mixing arrangement could be implemented in various ways. It could comprise one part or many separate parts. For example, it could be a plow-like or flange-like arrangement. When the growing chamber is rotated, the mixing arrangement mixes the matter, such as food, inside the growing chamber and lifts it and drops over the growing plates 306.

Figure 4A:
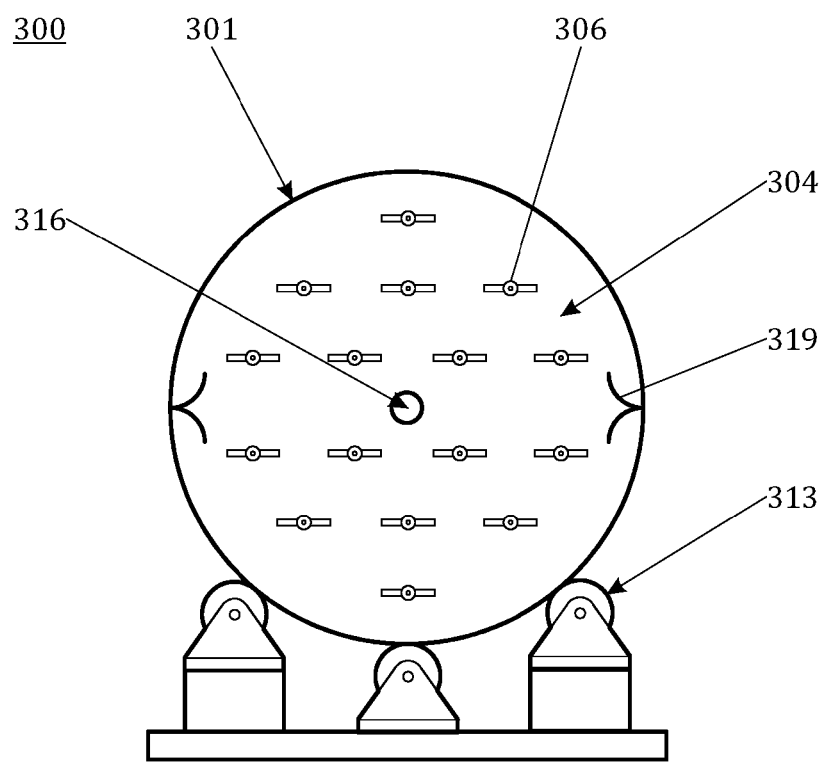
FIG. 4A shows a cross section of the apparatus of FIG. 3, when the casing is in one position.
Figure 4B:
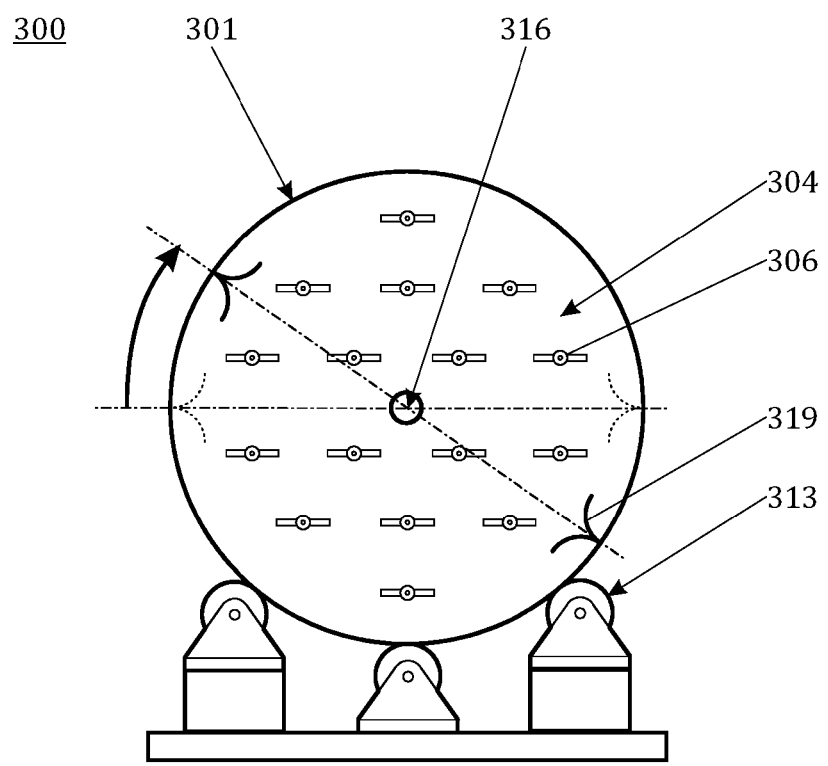
FIG. 4B shows a cross section of the apparatus of FIG. 3, when the casing is in another position.

In FIG. 4A, the casing 301 is in one position. The growing plates 306 are in a horizontal position. In FIG. 4B, the casing 301 has rotated to another position. The growing platform is immobile in relation to the casing. The growing platform moving arrangements compensate this movement and rotate the growing platform in such a way that the growing plates remain in a horizontal position.

Figure 5:
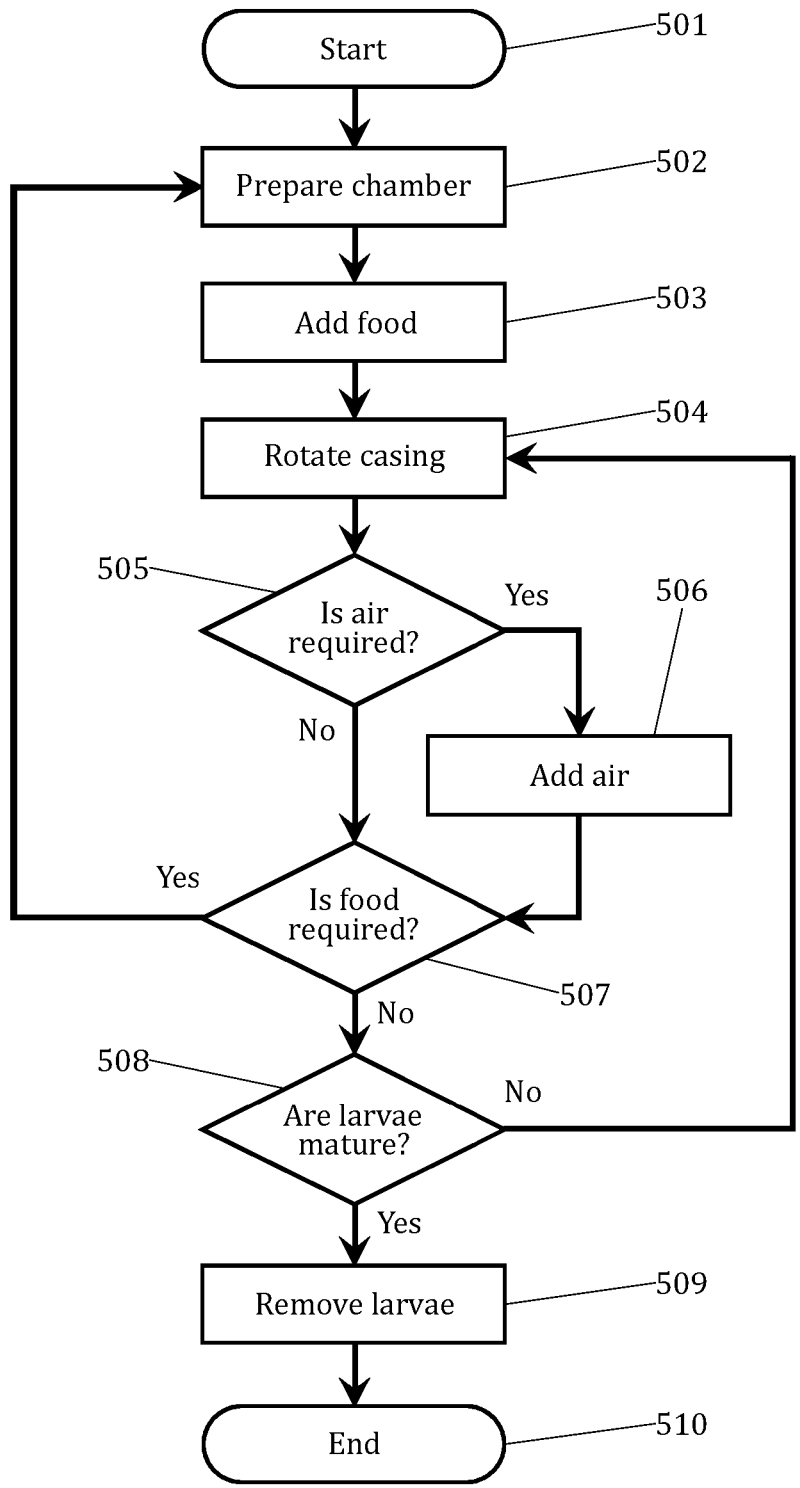
FIG. 5 shows an example of a method according to the present disclosure as a flow chart.

FIG. 5 shows an example of a method according to the present disclosure as a flow chart.

In the method an apparatus according to the present disclosure is used. In this example, the invertebrates to be grown are larvae of the housefly (of the order Diptera, *Musca domestica*). If some other species of invertebrate is used, the steps could be slightly different.

The method for growing invertebrates is started at the step 501.

At step 502, the growing chamber is prepared for growing process. This could include cleaning and sterilizing the growing chamber. Also, larvae are added in this step with some medium to start the growing.

At step 503, a liquid food medium is added to the growing chamber. The food medium is, for example, a mixture of solid food matter and water. The amount of food is such that when it is spread over the walls and the growing plates in step 504, there are no or few areas where anaerobic areas could form. The young larvae are mixed in said liquid food medium when the food is added for the first time in the growing process.

At step 504, the casing is rotated in such a way that the liquid food medium spreads evenly over the walls and the growing surfaces inside the growing chamber.

At step 504, the casing is rotated in such a way that the growing plates will change their horizontal positions and the food medium and other materials inside the growing chamber are mixed and spread over the surface of the walls and the growing plates.

At step 505, it is checked if breathing air is needed. If the air should be changed, it is done at step 506.

At step 506, the breathing air is changed in the growing chamber. New air is blown into the lower part of the growing chamber. The oxygen-rich air flows between the growing plates. The used air is removed from the upper part of the growing chamber. It must be noted that if the casing, and at the same time the growing chamber, is arranged to be rotated, the airing process is done when the inlet and outlet holes for air are in a suitable position. Airing can be done also in different ways.

If the air does not need to be changed at step 507, it is checked if more food is required. If more food is required, it is done at step 503.

If no food or air is required, at step 508 it is checked if the larvae have matured to the desired size. When the larvae are mature, they are removed from the growing chamber by injecting water into the growing chamber and flushing it through outlet hole at step 509.

If the larvae are not mature, the casing is rotated. This is done at step 504.

At step 510, the method for growing invertebrates is ended.

It must be noted that the previous steps could be executed in a different order or some steps are executed simultaneously. Naturally, the method could include steps that are not described here like, for example, washing the interior of the growing chamber during the growing process. Also, many steps could be implemented differently when growing different species or using a different apparatus.

Some advantageous embodiments of the method and apparatus according to the present disclosure have been described above. The present disclosure is however not limited to the embodiments described above, but the inventive idea can be applied in numerous ways within the scope of the claims.

The invention claimed is:

1. An apparatus for growing invertebrates that breathe gas comprising:
 a casing having a first end and a second end, the casing configured to rotate about a rotation axis between the first end and the second end;
 a growing chamber arranged inside said casing, the growing chamber comprising at least one growing platform; wherein
 the growing platform extends between the first end to the second end, and
 the growing platform is configured to rotate and comprises:
  one or more growing plates having a first end and a second end,
  a first growing plate surface and a second growing plate surface and wherein:
  the first growing plate surface is configured to be a growing surface for invertebrates and the growing platform is configured to maintain the first growing plate surface facing upwards even when the casing is rotated.

2. The apparatus according to claim 1, wherein the growing platform further comprises:
 a growing platform shaft extending between the casing first end and second end, and
 at least one growing plate fixed to the growing platform shaft.

3. The apparatus according to claim 1, wherein the growing platform comprises a first growing platform shaft and a second growing platform shaft, the first growing platform shaft arranged at a first end of the casing and the second growing platform shaft arranged at a second end of the casing and the at least one growing plate is fixed between the first growing platform shaft and the second growing platform shaft.

4. The apparatus according to claim 1, wherein on the first growing plate surface is arranged a shape or shapes configured to keep invertebrates on the growing surface, and wherein the shape or shapes comprise at least one of grooves and recesses.

5. The apparatus according to claim 1, wherein:
 the casing comprises an elongated structure having a longitudinal axis longer than a diameter of the casing, and
 the rotation axis of the casing is parallel to the longitudinal axis of the growing platform or growing platforms.

6. The apparatus according to claim 1, further comprising a locking arrangement configured to fix the growing platform to be immobile in relation to the casing such that the first growing plate surface keeps facing upwards when the casing is rotated.

7. The apparatus according to claim 1, further comprising a casing rotating arrangement and a growing platform moving arrangement wherein the casing rotating arrangement and the growing platform moving arrangement are synchronized such that the first growing plate surface keeps facing upwards when the casing is rotated.

8. The apparatus according to claim 1 further comprising means for at least one of air and a gas to be blown into the growing chamber such that the gas flow is tracking at least some part of the first growing plate surfaces.

9. The apparatus according to claim 1, wherein:
 at least one part of the inner surface of the casing forms the growing chamber inner wall; and
 at least one mixing arrangement is arranged on the inner surface of the casing, the at least one mixing arrangement comprising at least one flange configured to mix and lift food for the invertebrates from a bottom of the growing chamber when the casing is rotated.

10. The apparatus according to claim 1, further comprising a central shaft configured to be at least partly hollow and arranged to transport at least water into the growing chamber.

11. The apparatus according to claim 1, wherein:
 at least part of at least one of the first end of the casing or the second end of the casing is movable in relation to the casing; and
 the at least one growing platform is fixed to at least one of the first end of the casing and the second end of the casing.

12. The apparatus according to claim 1, wherein the growing plate is configured to be rotatable at least to a position where the growing plate surfaces are vertical.

13. The apparatus according to claim 12, wherein the growing platform is configured to follow the rotation of the casing and the growing plate is configured to be turned when the growing platform is in a lower position in relation to the casing.

14. A method for growing gas breathing invertebrates in a chamber comprising a casing and a first growing plate, the method comprising the steps of:
 introducing food into the growing chamber;
 maintaining the first growing plate surfaces in an upward-facing position so as to increase an inner surface area of the growing chamber;
 adding the invertebrates into the growing chamber at at least one of before, during or after injecting the food; and rotating the casing so that the food spreads at least partly over surfaces of an inner wall of the growing chamber and drip onto the first growing plate surfaces.

* * * * *